US009533158B2

(12) United States Patent
Min

(10) Patent No.: US 9,533,158 B2
(45) Date of Patent: Jan. 3, 2017

(54) SYSTEM AND METHOD FOR MONITORING PATIENT CONDITION USING ATRIAL TIMING CHARACTERISTICS

(75) Inventor: Xiaoyi Min, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 1925 days.

(21) Appl. No.: 12/333,176

(22) Filed: Dec. 11, 2008

(65) Prior Publication Data

US 2010/0152802 A1    Jun. 17, 2010

(51) Int. Cl.
| | |
|---|---|
| *A61N 1/00* | (2006.01) |
| *A61N 1/37* | (2006.01) |
| *A61B 5/0452* | (2006.01) |
| *A61N 1/368* | (2006.01) |
| *A61N 1/362* | (2006.01) |

(52) U.S. Cl.
CPC .............. *A61N 1/37* (2013.01); *A61B 5/0452* (2013.01); *A61N 1/368* (2013.01); *A61N 1/3627* (2013.01)

(58) Field of Classification Search
CPC ................................ A61N 1/37; A61B 5/0452

USPC ......................... 607/9, 14, 4, 5; 600/515–518
See application file for complete search history.

(56) References Cited

U.S. PATENT DOCUMENTS

| 5,179,949 A  *  | 1/1993 | Chirife ............................... 607/9 |
| 5,184,615 A  *  | 2/1993 | Nappholz et al. ............... 607/14 |
| 2002/0099303 A1* | 7/2002 | Bardy ............................ 600/515 |

* cited by examiner

*Primary Examiner* — Edward Moran
*Assistant Examiner* — Nadia A Mahmood

(57) ABSTRACT

A system and method for using an implantable cardiac stimulation device to monitor a patient for the progress of an existing condition and/or early detection of an emerging condition based, at least in part, on measuring and evaluating the timing characteristics of the patient's atrial activity. The atrial timing characteristics are used as indicators or predictors of conditions of interest, such as heart failure (HF) and atrial fibrillation (AF). In certain implementations, the system can determine discriminating indicators of a predominant underlying cause of a condition, such as between vagal and non-vagal AF, as an indicator of a suggested therapy. The system can store data corresponding to the observed atrial timing for trending analysis as well as transmit data for offline analysis, such as via an external device.

13 Claims, 8 Drawing Sheets

SYSTEM AND METHOD FOR MONITORING PATIENT CONDITION USING ATRIAL TIMING CHARACTERISTICS

BACKGROUND OF THE INVENTION

Field of the Invention

The invention relates to the field of implantable cardiac stimulation devices and, more especially, to implantable cardiac stimulation devices and methods of use of such devices to observe and evaluate timing of atrial events, for example for monitoring for onset of atrial fibrillation (AF) and/or the progression of heart failure (HF).

Description of the Related Art

Heart failure (HF) refers broadly to a variety of health ailments related generally to weakening and/or damage to the heart and characterized by a reduction in the mechanical ability of the heart to deliver an appropriate supply of blood. Heart failure can encompass an enlargement/dilation of the heart muscle, a degradation of the contractile properties of the heart, and/or a reduction in the synchrony among the heart chambers during cardiac contractions. Heart failure can also correspond to damage to or deterioration of heart valves and other structural conditions which reduce the cardiac output. Heart failure is also frequently found coincident with a variety of cardiac arrhythmias.

Heart failure can be of a varying degree of severity, ranging from the least severe where the HF condition may be detected upon clinical evaluation and wherein overt symptoms may only be noticed during strong physical exertion to the most severe conditions of HF, wherein the patient experiences severe symptoms even when fully resting. A variety of therapies are available to treat HF and the severity and progress of an HF condition is a valuable indicator for the patient's overall health status. Thus, it will be appreciated that being able to readily identify and characterize either the onset of an HF condition or the progression/status of a known HF condition can provide a valuable diagnostic tool to a clinician to provide more effective therapy to the patient.

A variety of examinations and observations can be utilized by a clinician to evaluate the existence or progression of an HF condition. A physical examination and interview of the patient can reveal, for example, edema and/or weight gain caused by fluid accumulation, which is a frequent symptom of HF. Shortness of breath is also a common symptom of HF and an interview of the patient and examination can reveal the severity of and conditions under which the shortness of breath occurs. An examination can also reveal a third heart sound (frequently referred to as S3) as well as a sound of fluid in the lungs during inspiration (rales), either of which are common symptoms of HF. A clinician may also observe enlargement of the jugular vein in the neck region (jugular venous distention) and/or enlargement of the liver (hepatomegaly). This may be coupled with a hepatojugular reflex wherein an enlarged liver which is subjected to manual pressure forces more blood into the jugular veins, causing them to become even more enlarged.

Several diagnostic tests are also useful in diagnosing HF, including chest x-rays which can reveal pulmonary edema, an enlarged heart, and pleural effusion. Electrocardiograms (EKGs) are also useful for their ability to detect the presence of a heart attack, cardiac ischemia, abnormal heart rhythms, and/or an enlarged heart. Echocardiograms are additional useful diagnostic tools which can determine the amount of blood ejected from the heart with each heartbeat, and more particularly, the proportion of blood ejected which is typically referred to as the ejection fraction. The ejection fraction is a useful way to quantitatively characterize the efficiency of the heart which is closely related to the presence or severity of a HF condition. For a normal healthy person, the ejection fraction typically is in the range of approximately 55 to 75%. A person suffering from HF would typically have a lower ejection fraction with a more depressed ejection fraction indicating a more severe HF condition. Echocardiograms can also diagnose particular causes of HF, including heart valve abnormalities, pericardial abnormalities, congenital heart disease, and/or an enlarged heart. Echocardiograms can also show if the contraction of the heart itself is abnormal, such as in wall motion abnormalities.

While these clinical observations and diagnostic tests offer valuable information for diagnosing the presence/progress of a heart failure condition, they suffer from the disadvantage of requiring the direct intervention of a highly trained clinician. The aforementioned patient observations require the training and judgment of a skilled clinician to accurately diagnose the patient observations. The aforementioned diagnostic tests, in addition to requiring the services of a skilled clinician to perform the tests, also typically require that the tests take place in a clinical setting. Diagnostic equipment such as chest x-ray and echocardiogram machines are large, complex, and relatively expensive pieces of equipment which are neither portable nor economical for the dedicated service of a single patient. Thus, the aforementioned observations and diagnostic tests are not suitable for frequent ongoing diagnosis of a patient's HF condition but rather are more suitable to serve patients at scheduled clinical appointments.

Another drawback to clinical evaluations is that emerging conditions can occur intermittently and may not manifest themselves during the limited clinical session, thus making proper diagnosis problematic. Early diagnosis and initiation of appropriate therapy can be very valuable in mitigating a new or changing condition. For example, monitoring intra-atrial conduction time (IACT) provides a surrogate for progression or remodeling such as LA dilation, LV functions and Mitral Valve Regurgitation (MR). Early identification of onset of atrial fibrillation (AF) as well as establishing the predominant cause of the AF can be very beneficial in mitigating the effects of the AF. AF refers to a rapid, generally chaotic, atrial arrhythmia with dramatically reduced pumping efficiency. Early detection of AF, for example at a paroxysmal stage, can enable early provision of therapy to prevent paroxysmal AF from possibly progressing to permanent AF. Establishing a predominant cause of a patient's AF is important as certain treatments for certain categories of AF are contraindicated for other categories of AF.

For example, the heart's natural rate control system includes inputs from two branches of the autonomic (involuntarily controlled) nervous system. The cardiac nerve provides a sympathetic branch of the autonomic nervous system; stimulation by the cardiac nerve will speed the heart rate up (adrenergically mediated). The vagus nerve provides a parasympathetic branch of the nervous system, wherein vagal activity slows the heart rate. These two physiologic controls respond to and balance the body's metabolic requirements, for example by speeding up blood flow during exercise or reducing it again afterwards. In a normal heart, the vagus nerve is active and provides a "vagal drive" to slow an otherwise faster intrinsic heart rate. Certain incidences of AF are considered to be largely vagally mediated as opposed to non-vagal or adrenergic AF. The importance of distinguishing AF which is vagally mediated from non-vagal AF is that, depending on the case, certain drug treatments that can be helpful in one case are in the other case unhelpful, and at worst harmful, to the patient's condition.

SUMMARY OF THE INVENTION

It will be appreciated that the ability to more frequently evaluate a patient, such as for the progression or current/recent status of a possibly changing HF condition and/or for onset of a new AF condition, on an ongoing manner without requiring the immediate attention of a skilled clinician and expensive complex diagnostic equipment, could provide valuable diagnostic information to more accurately and timely track the patient's condition. There is also a need for early detection of the onset of new conditions, such as AF, or worsening of LV dysfunctions, MR, and LA/LV dilation etc. There is also a need to identify an underlying cause of a condition, such as AF or LV remodeling. Thus, there is an ongoing need for a system and method of evaluating a patient's condition in a portable relatively inexpensive manner which would facilitate evaluation of the condition on a frequent ongoing manner and more particularly in intervals between clinical evaluations.

These needs are addressed by various embodiments of the invention which, in certain implementations, includes an implantable cardiac stimulation device which is configured to monitor and evaluate timing of atrial events for indications of the onset of new conditions and/or the progression of an existing condition. Certain cardiac arrhythmias indicate implantation of an implantable cardiac stimulation device to provide therapeutic stimulation for the patient's condition. Further configuration and use of an implantable cardiac stimulation device according to one or more embodiments of the invention can provide the ability to identify the onset of a new condition which had not previously been observed at the time of implantation or any subsequent follow-up evaluations. In certain embodiments, a cardiac stimulation device and use thereof can also discriminate between likely underlying or mediating factors in an onset condition. In yet other embodiments, a cardiac stimulation device and use thereof can track or monitor the progression of a known existing condition. The device can store information indicative of the progression which can be utilized, for example to reprogram the operating parameters of the device in accordance with the progression of the condition and/or modify/institute other therapy, such as a medication regimen.

Thus, one embodiment includes an implantable cardiac therapy device adapted for connection to at least one implantable lead having at least one stimulation electrode and to at least one sensor to thereby define at least one stimulation circuit and at least one sensing channel, the device comprising a controller configured to receive sensed signals from the at least one sensor, determine conduction timing characteristics of sensed signals corresponding to a patient's atrial activity, evaluate the conduction timing characteristics for surrogate indications of a change in the patient's condition indicating a change in their therapy by comparing one or more of the conduction timing characteristics to corresponding thresholds, and record data indicative of the indications of a change in the patient's condition when one or more of the conduction timing characteristics indicates a change in the patient's therapy.

Another embodiment includes a method of evaluating a patient's condition via use of an implantable cardiac therapy device, the method comprising implanting a cardiac therapy device, engaging the implantable device with at least one sensing electrode, sensing a patient's cardiac activity, including activity of the atria, via the therapy device, determining at least one atrial conduction timing characteristic at at least intervals of cardiac cycles via the device, storing the determined at least one determined at least one atrial timing characteristic in memory of the device, and comparing a record of the at least one atrial conduction timing characteristic over time with at least one corresponding threshold as a surrogate indicator of a change in at least one patient condition.

A further embodiment includes an implantable cardiac stimulation device comprising at least one lead adapted to be implanted within a patient so as to be able to deliver therapeutic stimulation to the patient's heart, at least one sensor that is adapted to sense signals indicative of electrical activity of the heart of the patient, and a controller that receives signals indicative of the electrical activity of the heart from the at least one sensor and selectively induces delivery of therapeutic stimulation to the heart of the patient via the at least one lead, wherein the controller evaluates at least one parameter of the signals received from the sensor that relates to the duration of the atrial activity to determine if signals corresponding to atrial activity of the heart are indicative that the heart is potentially developing a future dysfunction and wherein the controller records data indicative of the potential future dysfunction upon determining that the data is indicative thereof.

An additional embodiment includes an implantable cardiac stimulation device comprising at least one lead adapted to be implanted within a patient so as to be able to deliver therapeutic stimulation to the patient's heart, at least one sensor that is adapted to sense signals indicative of atrial activity of the heart of the patient, and a controller that receives signals indicative of the atrial activity of the heart from the at least one sensor and selectively induces delivery of therapeutic stimulation to the heart of the patient via the at least one lead, wherein the controller evaluates at least one timing parameter of the atrial signals to determine if the signals are indicative that the heart is potentially developing a future fibrillation condition and wherein the controller records data indicative of the potential future fibrillation condition upon determining that the data is indicative thereof. These and other objects and advantages of the invention will become more apparent from the following description taken in conjunction with the accompanying drawings.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
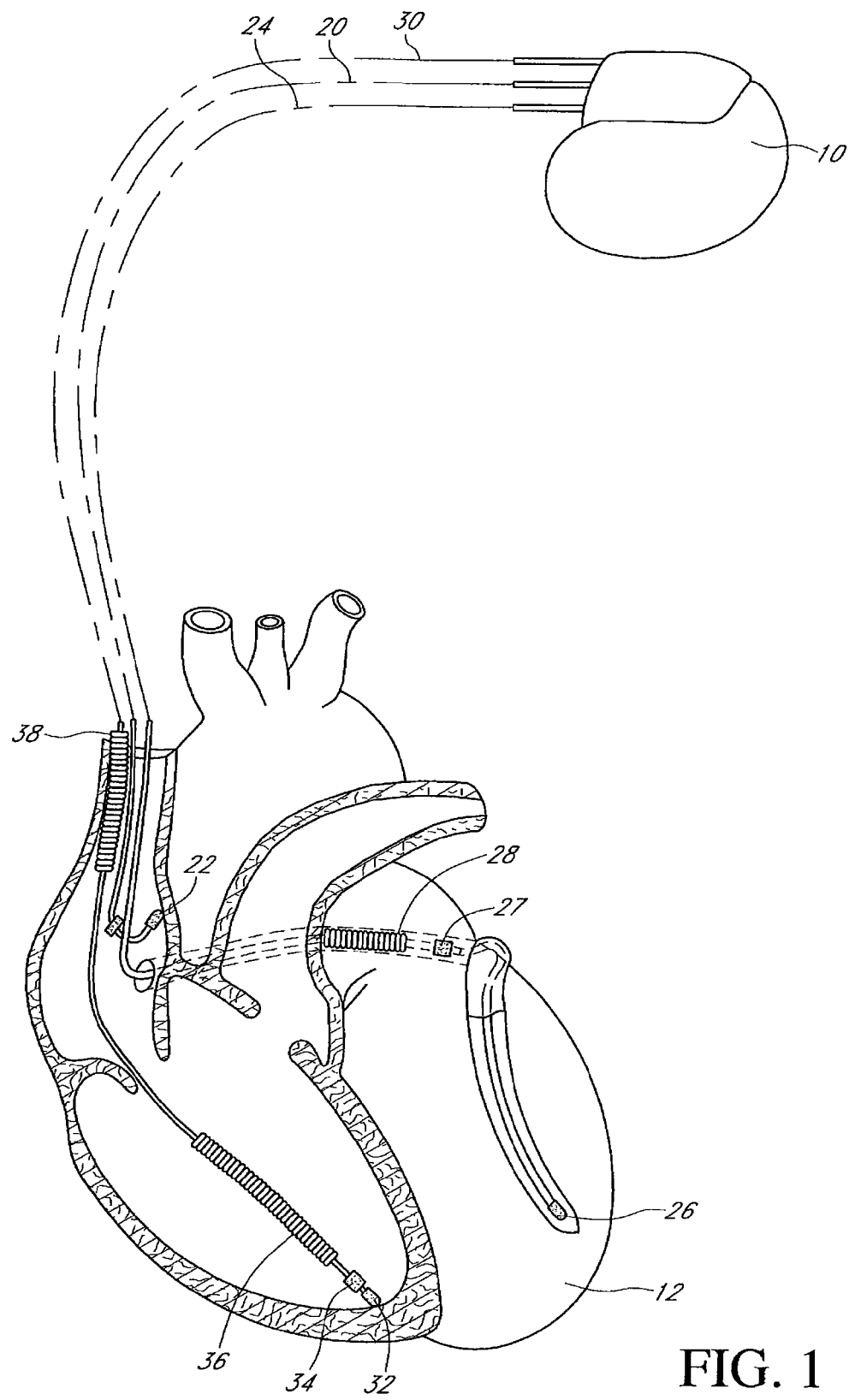
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
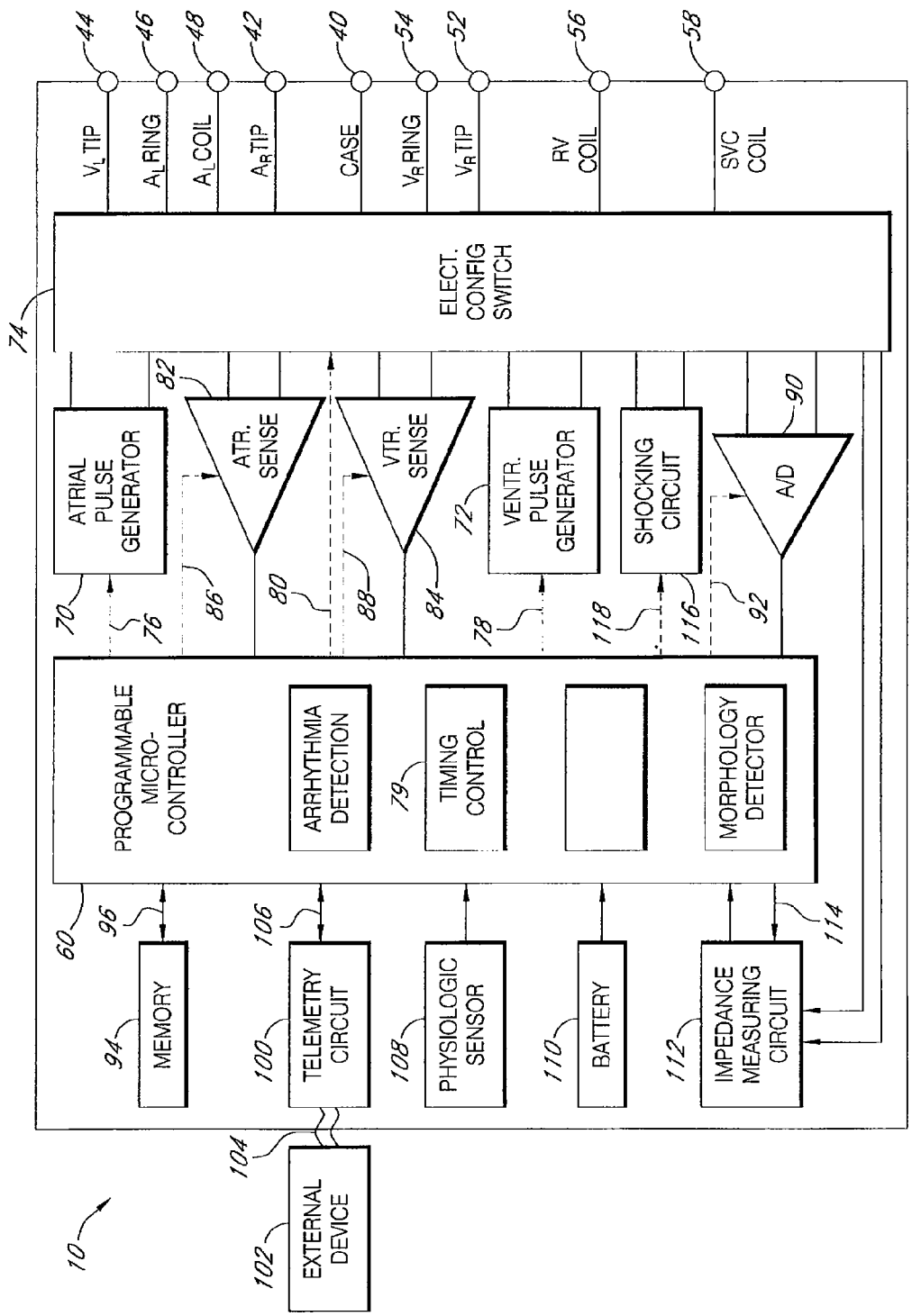
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/ defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Many patients have conditions which indicate that they be provided with a therapeutic cardiac therapy device. Embodiments of the invention are based at least in part on utilizing an implantable cardiac stimulation device, such as the device 10 previously described, for ongoing monitoring of the patient's condition. Certain embodiments utilize analysis based on sensing which is performed by the device 10 and can be utilized for other purposes, such as the determination of need for therapy delivery as previously described. Certain embodiments can also be utilized in addition to or as an alternative to other configurations of sensing to obtain desired measurements. Various embodiments are adapted for early detection of an emerging condition and to keep a record of data related to the emerging condition. These embodiments facilitate early detection of an emerging condition which may not manifest itself during a scheduled clinical evaluation. Certain embodiments also provide the ability to track or generate trend data, for example for monitoring for changes in a known or preexisting condition where the changes may indicate revision of a patient's therapy or other intervention.

Embodiments of the invention are based at least in part on measurement and analysis of timing characteristics of atrial activity. As previously described, an implantable cardiac stimulation device, such as the device 10 previously described, can provide a wide variety of sensing configurations, including configurations capable of sensing atrial activity. It will be understood that in certain implementations, a device 10 can provide the capability for sensing configurations which might not otherwise be utilized for a particular patient. Thus, in certain implementations, arrangements of one or more sensing electrodes are activated for measurement of the patient's atrial activity for further evaluation and these one or more arrangements can interact with detection thresholds which may not otherwise be utilized for the ongoing evaluation of the patient's cardiac activity, for example for determining delivery of pacing or shocking therapy.

In one embodiment, the device 10 is configured for attachment to the right atrial lead 20 including the right atrial tip electrode 22 as well as the coronary sinus (CS) lead 24 including one or both of the left atrial ring electrode 27 and left atrial coil electrode 28. In this embodiment, the right atrial tip electrode 22 is configured for implantation in the patient's right atrial appendage. Similarly, the left atrial ring electrode 27 and/or left atrial coil electrode 28 are configured for implantation adjacent the left atrium. In this embodiment, the electrodes 22 and 27 and/or 28 respectively, are positioned adjacent the right and left atria, respectively. Thus, in this embodiment, substantially direct measurements can be made such as of an interatrial conduction time or delay.

In another embodiment, the device 10 includes a superior vena cava (SVC) coil electrode 38. In this embodiment, the SVC electrode 38 is configured to be implanted proximally with respect to the atria and distally with respect to the ventricles. In this embodiment, the SVC electrode 38 can be utilized in a unipolar sensing configuration with respect to the housing or can 40 comprising a reference electrode to develop a pseudo surface ECG. This embodiment develops a composite signal representative of activity of both atria and with atrial activity preferentially sensed due to the configuration of the SVC electrode 38 for implanting more proximal the atria than the ventricles. It will be understood that in certain implementations, additional measures may be needed to suppress sensing of far field events to facilitate, at least temporarily, sensing of the atrial timing characteristics. For example, in certain implementations a programmed AV delay may need to be temporarily adjusted to a long enough value to avoid far field ventricle pacing from interfering with measurement of atrial activity, such as in measuring a P-wave duration.

Figure 3:
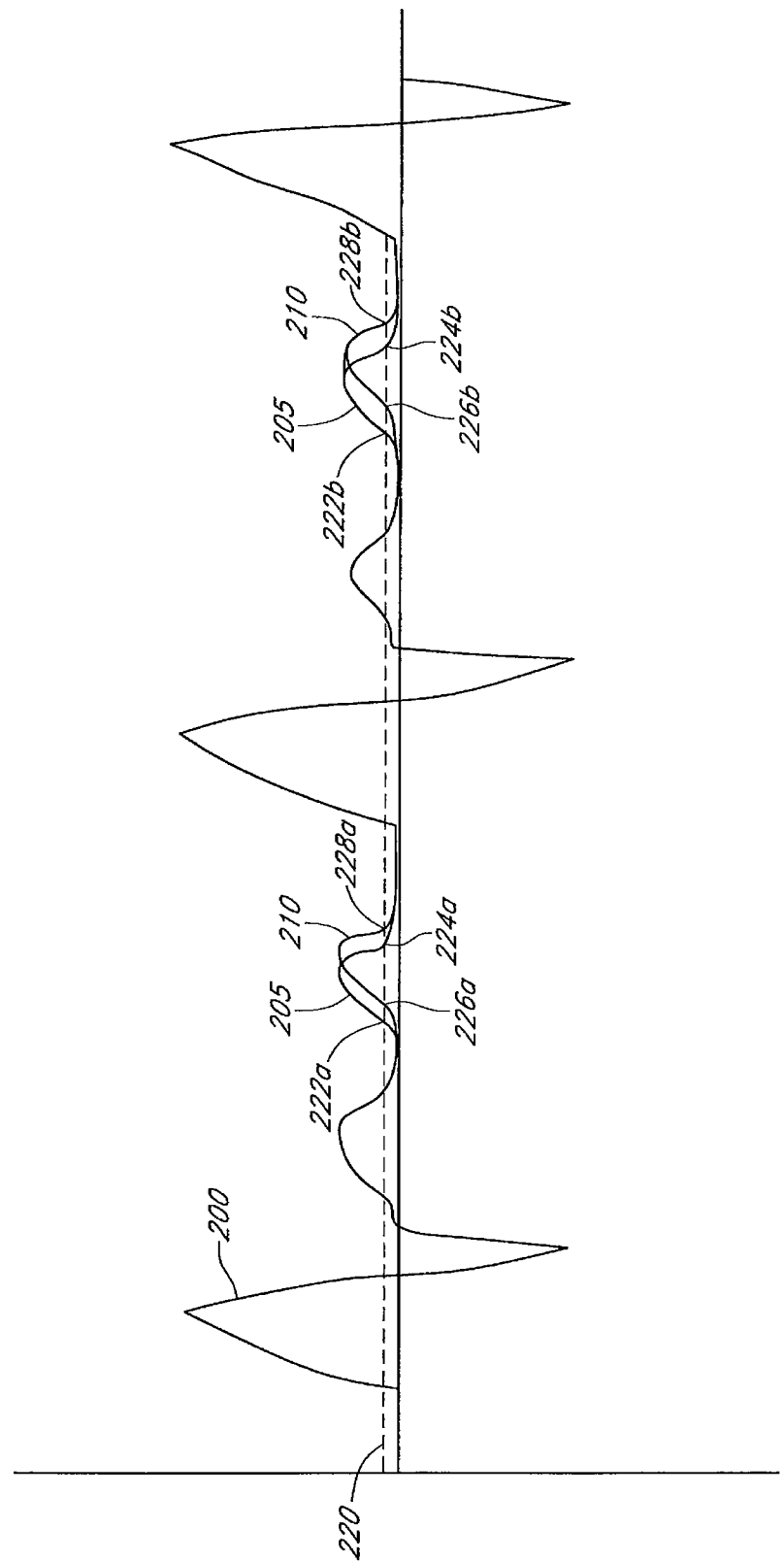
FIG. 3 is a waveform illustrating exemplary sensing of a patient's cardiac activity, including atrial activity via a plurality of sensing channels, according to one embodiment.
Figure 4:
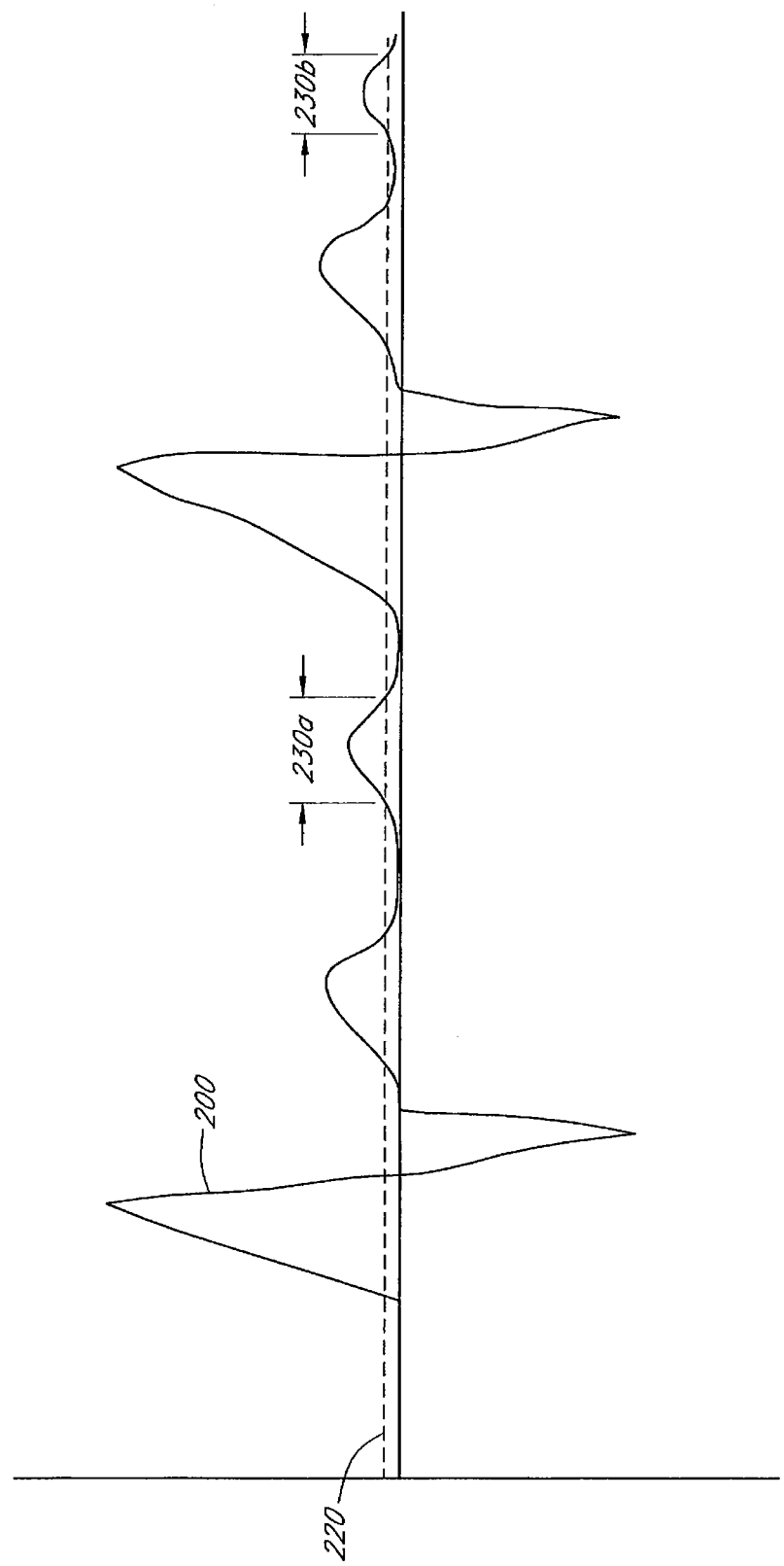
FIG. 4 illustrates a further exemplary waveform corresponding in this embodiment to a composite surface EGM waveform showing P, QRS, and T waves including timing characteristics of a patient's atrial activity.

FIG. 3 illustrates schematically one embodiment of a system and method for monitoring a patient's condition by evaluation of atrial timing characteristics. It will be understood that the illustration of FIG. 3 and the following FIG. 4 is schematic or illustrative in nature and should not be interpreted as accurately portraying the exact morphology, amplitude, or relative timing of actual measured events as implemented by a particular device and as programmed for an individual patient's needs and conditions.

FIG. 3 illustrates generally a composite waveform of signal contributions of a plurality of sensing channels including a first atrial channel 205 and a second atrial channel 210. For purposes of illustration and understanding, the constituent signals contributing to the composite waveform 200 are illustrated as merged into a single waveform trace for those portions of the composite waveform 200 not corresponding substantially to atrial activity. However, the first atrial channel signals 205 and second atrial channel signals 210 are illustrated separately when substantially corresponding to atrial activity, such as a P-wave, for a better understanding of this embodiment.

Further, the composite waveform 200 is illustrated with respect to a detection threshold 220. The detection threshold 220 corresponds to a selected or determined value preferably set a level to avoid interference from noise and further defining a detection threshold for atrial events of interest. In one particular embodiment, the detection threshold 220 is set at approximately 0.2 millivolts above an average noise level.

FIG. 3 further illustrates certain representative events sensed by the first atrial channel 205 and second atrial channel 210. In this embodiment, an initial first channel event 222a occurs as the P-wave sensed by the first atrial channel 205 initially rises above the detection threshold 220. A concluding atrial event 224a occurs as the P-wave sensed by the first atrial channel 205 subsequently drops below the detection threshold 220. Similarly, an initial atrial event 226a sensed by the second atrial channel occurs when the P-wave sensed by the second atrial channel 210 rises above the detection threshold 220. Similarly, a concluding atrial event 228a occurs as the P-wave as sensed by the second atrial channel 210 drops below the detection threshold 220.

Thus, in this embodiment, the two separate atrial channels 205, 210 can independently sense the initiation and conclusion of a P-wave as the sensed amplitude rises above and drops below a detection threshold 220. As the first and second atrial channels 205, 210 are configured for different arrangement during implantations, e.g., to sense from different locations within the patient's body, by determining the relative timing of these multiple events, 220a, 224a, 226a, and 228a, a measurement or determination of conduction delays can be determined. As there will be expected variations in both the electrochemical characteristics of the implanted location as well as the physical distance between the locations of multiple electrodes as implanted for different patients, evaluation of the relative timing between the multiple events will need to be adapted to the specific application. Adjustment/programming of the device 10 for a given application will be readily understood by one of ordinary skill as applied to the individual patient.

FIG. 3 also illustrates a second set of the events indicated as the reference designators 222b, 224b, 226b, and 228b. In various embodiments, a plurality of independent measurements and determinations of atrial timing characteristics can be made. For example, the timing difference between two of the events 222, 224, 226, 228 can be made for a plurality of cardiac cycles. These plurality of independent measurements can be evaluated and stored individually, be utilized to calculate an average, be used to calculate one or more deviation measures, and/or used to calculate a range of observed values.

FIG. 4 illustrates a further embodiment of a system and method for monitoring a patient's condition using atrial timing characteristics. In this embodiment, a composite waveform 200 represents a patient's cardiac activity. In this embodiment, the composite waveform 200 represents the composition of a plurality of separate sensing channels or a single sensing channel providing a composite signal. As noted above, the illustration of FIG. 4 is schematic or illustrative in nature and should not be interpreted as being accurately to scale with respect to the particular amplitudes, morphologies, or relative timing of a given patient.

In this embodiment, an atrial event duration 230a and 230b is shown for two subsequent cardiac cycles and corresponding to the patient's P-wave. The atrial event duration 230a, 230b corresponds to the interval or width over which the composite waveform 200 initially exceeds and subsequently decreases below a detection threshold 220. The atrial event duration 230 corresponding generally to the width of the patient's P-wave can be evaluated as a surrogate or indicator for a variety of patient conditions. This aspect of the invention will be described in greater detail below.

Figure 5:
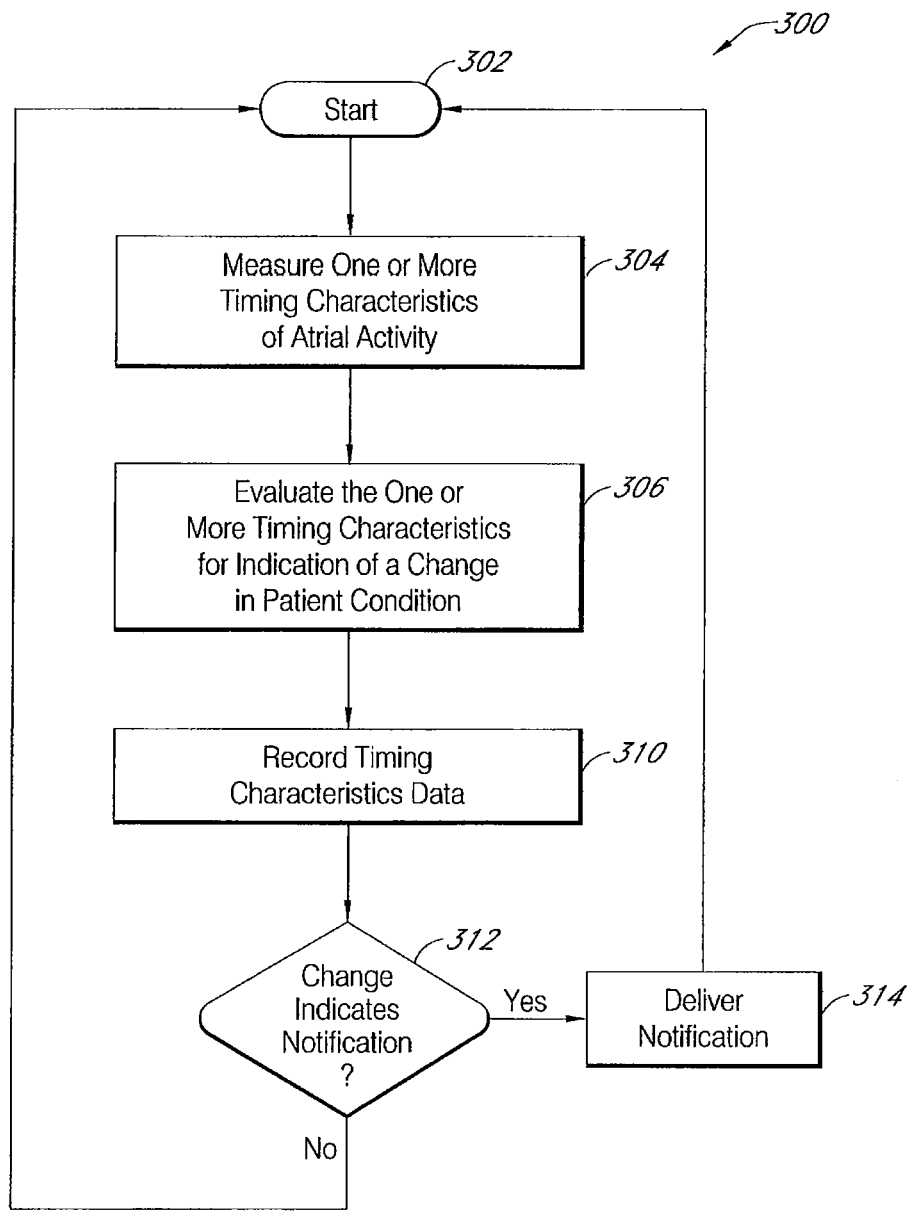
FIG. 5 is a flow chart of one embodiment of a system and method for evaluating a patient's condition via measurement and evaluation of their atrial timing characteristics.

FIG. 5 illustrates a flowchart of one embodiment of a system and method 300 for utilizing atrial timing characteristics for evaluation of a patient's condition. The system and method 300 begins in this embodiment in a start block 302. The start block 302 refers generally to the previously described ongoing operation of the device 10 including monitoring the patient's cardiac activity and generation and delivery of indicated therapy. In at least certain aspects, further blocks of the system and method 300 would proceed in parallel with other ongoing operations of the device 10 and these other operations are not illustrated in detail in FIG. 5, but rather generically as block 302 for ease of understanding.

Following from the start block 302 occurs a measurement block 304 wherein one or more timing parameters or characteristics of the patient's atrial activity are measured. The measurement of block 304 can proceed in a variety of manners depending on the requirements and indications of a particular application. In certain embodiments, the measurement of block 304 proceeds on a substantially constant basis in a similar manner to other sensing or measurement operations of the device 10. In other embodiments, the measurement of block 304 proceeds on a regular periodic basis, such as hourly, daily, weekly, etc. In yet other embodiments, the measurement of block 304 can be triggered asynchronously, for example upon receipt of an initiating command from an external device and/or by detection by the device 10 of conditions indicating initiation of the system and method 300. The measurements of the one or more timing characteristics of the patient's atrial activity performed in block 304 would generally correspond to one or more of the events 222, 224, 226, 228, and/or duration 230 previously described and illustrated with respect to FIGS. 3 and 4.

Following from the measurement of block 304 proceeds an evaluation block 306 wherein the one or more timing characteristics are evaluated for indications of a change in the patient's condition. For example, in one embodiment, the atrial event duration 230 corresponding generally to the patient's P-wave width can be evaluated in block 306 for indications of occurrence of AF. For example, in a normal healthy patient, intrinsic P-wave duration is usually in the range of approximately 60-80 milliseconds in length. Absent HF or certain AF conditions, a patient's atrial activity is generally in the range of approximately 50-60 milliseconds between the initiation of an atrial pacing pulse to the end of the evoked atrial depolarization.

If, however, atrial event durations 230 are measured of approximately 110-130 milliseconds or more, this can be interpreted in block 306 as predictive for occurrence of AF when the atrial event durations 230 correspond to an intrinsic activity. In the case where the atrial event duration 230 corresponds to evoked activity, a criterion of approximately 160 milliseconds can be utilized as a threshold for predicting occurrence of AF. Alternatively the atrial event duration for estimating intra-atrial conduction time (IACT) can be replaced by measuring LA activation from a LV lead or a LV lead with multi-pole electrodes.

In one embodiment, atrial event durations 230 in the range of approximately 110-130 ms can be further interpreted as indicative of vagally mediated AF. Atrial event durations 230 in the range of approximately 110-190 ms can be further interpreted as indicative of non-vagally mediated AF (see FIG. 6). As there is overlap in the exemplary ranges for values of approximately 110-130 ms, further evaluation, such as determination of average values of multiple atrial event durations 230 and determination of variance can be used to further discriminate between vagally and non-vagally mediated AF. Non-vagally mediated AF tends to exhibit a wider variance range of atrial event durations 230 than for vagally mediated AF.

Similarly, the evaluation of block 306 can be further utilized to characterize the progression of an existing condition. For example, many known HF patients would be expected to exhibit an atrial event duration 230 in the range of approximately 100-150. However, the system and method 300 can be utilized to generate and record trend data to alert the patient and/or attending clinical personnel to an observed change in the patient's status. For example, in one particular embodiment, a HF patient may have exhibited a history of atrial event durations 230 of approximately 100-110 milliseconds in duration. If however in an iteration of block 306 the system 300 determines that the patient is exhibiting atrial event durations 230 in the range of 140-150 milliseconds, the system can evaluate in block 306 that this is indicative of a change in the patient's HF status which may indicate revision or adjustment of one or more aspects of their therapy regimen. IACT can be used in combination with other variables such atrio-ventricular conduction delay, trans-thoracic impedance change, cardiac impedance, evoked response and others to track HF status/progression.

In a further block 310, the system and method 300 records or stores timing characteristic data as developed in the block 304. While illustrated in FIG. 5 as following block 306, it will be understood that the recording or storage block 310 can occur before and/or in parallel with an evaluation block such as the block 306. In the recording block 310, the system and method 300 can record a variety of data corresponding to the measurements and/or evaluation of the patient's condition. For example, in certain embodiments in order to conserve limited storage capacity, the storage block 310 may only record summary data or characterizing data. For example, in certain embodiments the storage or recordation of block 310 includes storing of a running average rather than each of a plurality of individual measurements. In other embodiments, the system and method proceeds with measurement and evaluation of the patient's condition on a more frequent basis than an update or storage of the measurement and evaluation, as in block 310. For example, in one implementation the system and method 300 performs hourly evaluations of the timing characteristics of the patient's atrial activity, however, only stores representative data of this measurement and evaluation on a daily basis.

In this embodiment, the system and method 300 also includes a decision block 312 wherein a determination is made as to whether the measurements and evaluations of the patient's condition indicate generation of a notification signal. For example, in certain embodiments, the system and method 300 can detect onset or emergence of a previously undetected condition, such as onset of AF. In other embodiments, the evaluation of block 306 can indicate an onset condition, such as AF, but be indeterminate as to the predominate cause. In this embodiment, the decision of block 312 can indicate notification for further diagnosis. In other embodiments, the decision of block 312 can correspond to a patient's condition changing to an extent that revision in their therapy is indicated.

Thus, if block 312 determines that notification is indicated, an optional subsequent block 314 can occur wherein notification is delivered. The notification of block 314 can comprise generation of a vibration which can be tactilely and/or audibly noticed by the patient to alert them to the need to contact their physician for further follow-up. In another embodiment, a notification can be delivered in block 314 via the implantable device 10 communicating with an external device 102 to alert a physician or other attending clinical personnel to the observed characteristics. These aspects of the invention facilitate early detection of an onset condition and early initiation of appropriate therapy to improve the likelihood of successfully mitigating the onset condition.

Figure 7:
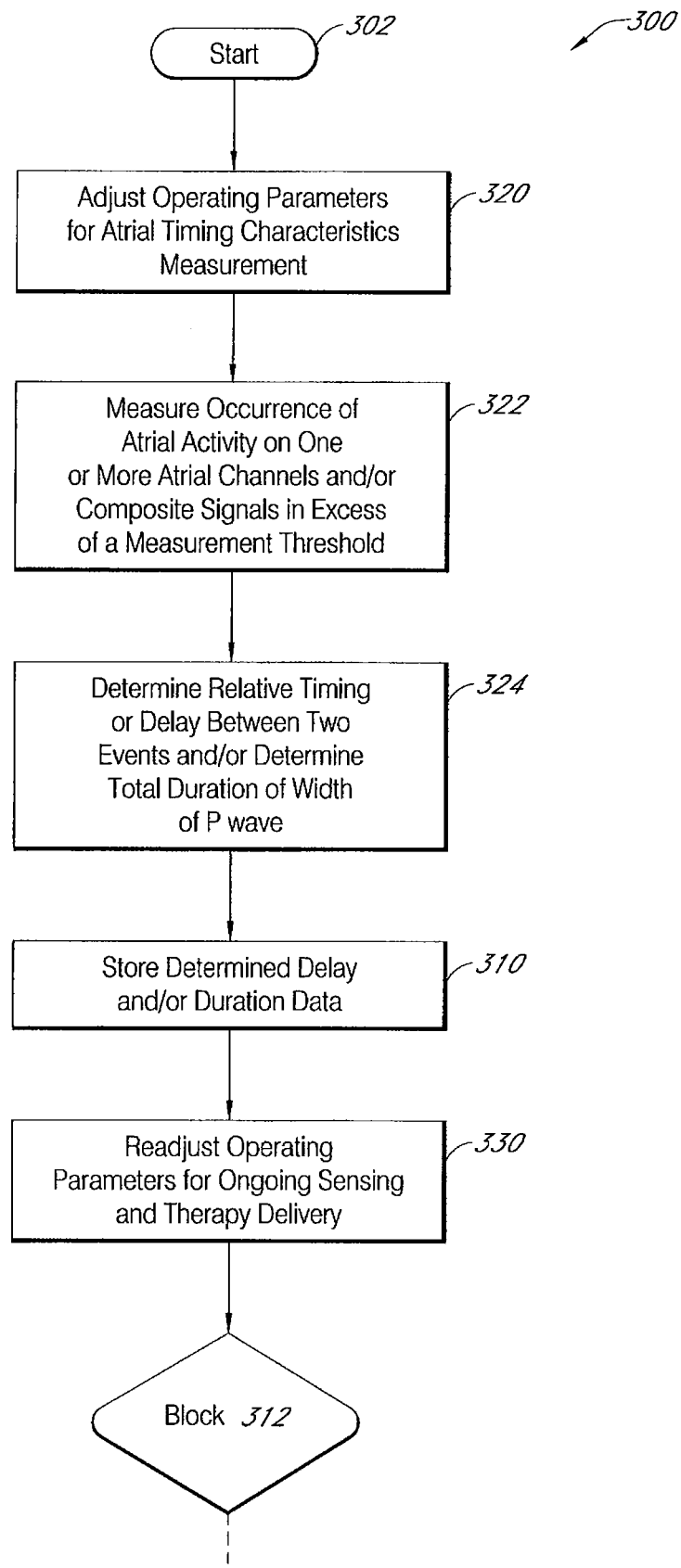
FIG. 7 is a flow chart of a further embodiment of a system and method for evaluating a patient's condition via measurement and evaluation of their atrial timing characteristics.

FIG. 7 illustrates a further embodiment of a system and method 300 for utilizing atrial timing characteristics for monitoring and evaluating a patient's condition. In this embodiment, the method 300 begins in a start block 302 substantially similar to the block 302 previously described with respect to FIG. 5. Following from the start block 302 is an adjustment block 320. In the adjustment block 320, one or more operating parameters of the device 10 are adjusted to facilitate measurement of one or more atrial timing characteristics. In this embodiment, certain operating characteristics of the device 10 may impede or interfere with accurate measurement of the patient's atrial timing characteristics. The adjustment provided by block 320 provides at least temporary modification of these operating parameters to facilitate measurement. For example, an AV delay programmed value appropriate for otherwise ongoing operation of the device 10, as in block 302, may interfere with accurate measurement of the patient's atrial timing characteristics.

Thus, in one embodiment the adjustment block 320 includes temporary elongation of the AV delay to avoid or reduce far field ventricular pacing events from interfering with measurement of the patient's P-wave data. Similarly, adjustment or variation in one or more blanking and/or refractory periods can be performed in block 320 on a temporary basis to facilitate more accurate measurement.

Figure 8:
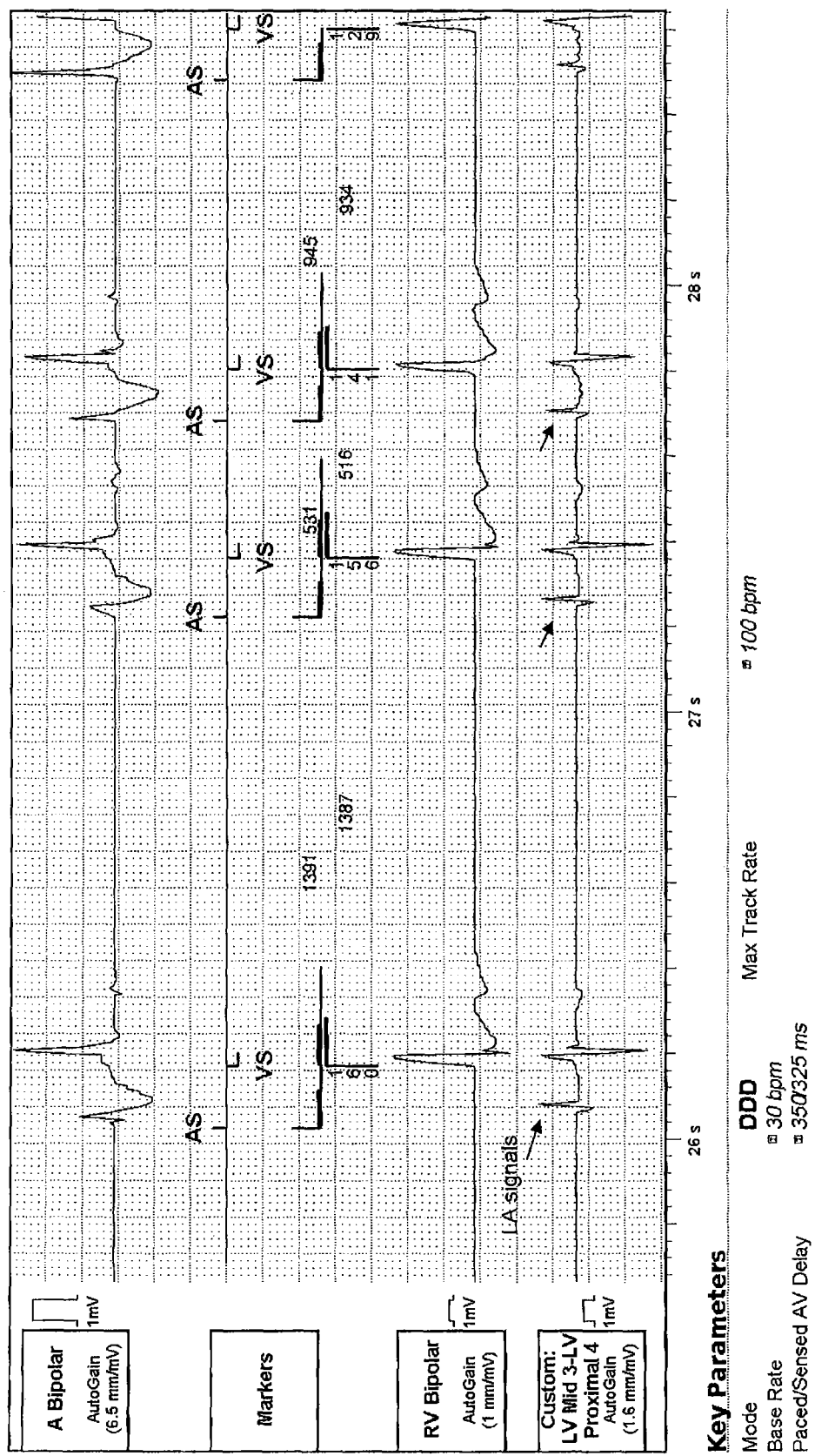
FIG. 8 illustrates waveforms indicative of additional embodiments of sensing of a patient's cardiac activity that can include intracardiac electrogram (IEGM) sensing via a plurality of sensing channels.

In another embodiment, IACT can be measured more directly, for example through LA activation signals by using a LV lead or a LV lead with multi-pole electrodes, for example as indicated by the arrows in FIG. 8. FIG. 8 illustrates exemplary animal based IEGM waveforms showing atrial and ventricular signals. The arrows indicate one embodiment of custom signals comprising a LV mid 3 to LV proximal 4 sensing vector.

Following from block 320 are blocks 322 and 324 wherein the occurrence of atrial activity is measured on one or more independent atrial channels and/or from a composite signal. The measurement is in certain embodiments performed with reference to a measurement threshold 220 wherein occurrence of the atrial activity is defined by signals exceeding or falling below the measurement threshold 220. The determination of relative timing of block 324 can be defined as a difference between initial observation of an event, such as the events 222 observed by a first atrial channel 205 and events 226 first observed by a second atrial channel 210. The total duration determined can correspond to the difference between initial observation on any channel and final conclusion of the event on any channel, such as a difference between the event 222 and 228. The duration can also correspond to the difference or duration observed by a composite signal. The system and method 300 in this embodiment also comprises a readjustment block 330. The readjustment block 330 essentially returns or readjusts the operating parameters of the device 10 for otherwise normal ongoing operation of the device 10, as for the operation indicated by block 302.

Figure 6:
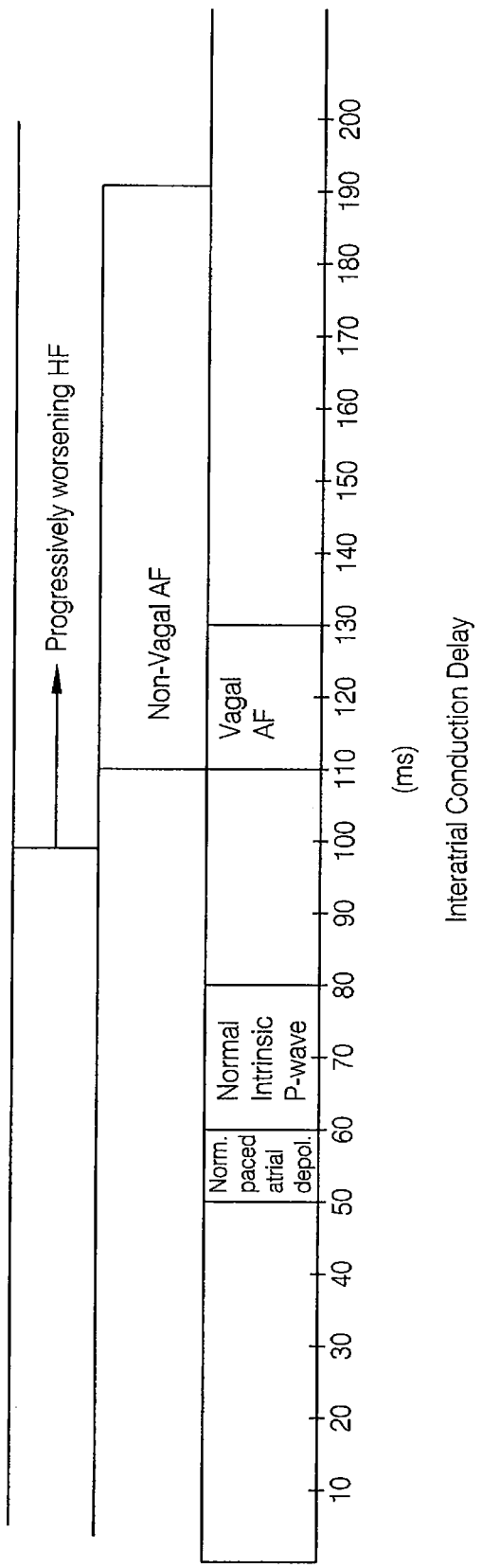
FIG. 6 illustrates one embodiment of exemplary threshold or discrimination parameters for evaluating a patient's condition based, at least in part, on measurements of timing characteristics of their atrial activity.

As indicated in FIG. 6, the system and method 300 also includes in this embodiment a storage block 310 and a decision block 312 substantially similar to that previously described with respect to FIG. 5. Again, while FIG. 6 illustrates block 310 as positioned between blocks 326 and 330, it will be understood that the storage of data provided in block 310 can occur in parallel, for example in parallel with the determination of block 324 or subsequently, for example following the readjustment of block 330.

Thus, various embodiments of the invention provide a valuable system and method for long-term observation of a patient both to track the progression of an existing condition as well as to monitor for the emergence of a condition which had not previously been observed. The system and method can be relatively inexpensively implemented via software modification of existing hardware platforms. The system and method can be implemented to perform measurements and evaluations on a periodic or non-continuous basis to reduce the burden of resources which could be utilized for other purposes while maintaining the benefit of extended long-term observation of a patient outside of schedule clinical evaluations. The system and method can further develop indications of new or changing conditions early to facilitate earlier modification and/or initiation of therapy to improve likelihood of more effectively treating the condition.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A method of evaluating a patient's condition via use of an implantable cardiac therapy device, the method comprising: sensing a patient's cardiac activity, including activity of the atria, via the therapy device;
   determining an interatrial conduction delay via the device;
   storing the interatrial conduction delay in memory of the device;
   comparing a record of the interatrial conduction delay over time with a corresponding threshold as a surrogate indicator of atrial fibrillation
   determining whether any change indicated warrants active notification of the change, and
   delivering a notification signal to alert at least one of the patient and attending clinical personnel of the indicated change when active notification is warranted;
   delivering stimulation to the heart by a lead based on the comparison of the record.

2. The method of claim 1, wherein the at least one patient condition comprises a known disease condition and wherein the change comprises a defined variation of the interatrial conduction delay from a previously determined value of the interatrial conduction delay.

3. The method of claim 1, wherein the atrial fibrillation was a previously unobserved patient condition.

4. The method of claim 3, further comprising characterizing a range of the record of the interatrial conduction delay and comparing the record with predetermined ranges of the interatrial conduction delay wherein the predetermined ranges are indicative of likely mediating factors of the previously unobserved condition.

5. The method of claim 3, further comprising determining a variation of the interatrial conduction delay and comparing the determined variation with predetermined variations of the interatrial conduction delay wherein the predetermined variations are indicative of likely mediating factors of the previously unobserved condition.

6. The method of claim 1, wherein storing the interatrial conduction delay in memory of the device comprises storing a running average of the interatrial conduction delay.

7. The method of claim 1, wherein the determining interatrial conduction delay at via the device is performed on a regular periodic basis.

8. An implantable cardiac stimulation device comprising:
   at least one lead adapted to be implanted within a patient so as to be able to deliver therapeutic stimulation to the patient's heart;
   at least one sensor that is adapted to sense signals indicative of electrical activity of the heart of the patient; and
   a controller that receives signals indicative of the electrical activity of the heart from the at least one sensor and processes the sensed signals to determine an interatrial conduction delay, wherein the controller selectively induces delivery of therapeutic stimulation to the heart of the patient via the at least one lead, and wherein the controller evaluates a timing parameter related to the interatrial conduction delay to determine if signals corresponding to atrial activity of the heart are indicative that the heart is potentially developing a future dysfunction and wherein the controller records data indicative of the potential future dysfunction upon determining that the data is indicative thereof; and
   wherein the at least one parameter of the atrial signals comprises one or more of a P wave duration and an interatrial conduction delay sensed at a left atria (LA).

9. The device of claim 8, wherein the at least one lead includes a plurality of electrodes wherein at least some of the electrodes can be configured for delivering therapy to the heart of the patient or functioning as the at least one sensor sensing signals indicative of the electrical activity of the heart of the patient.

10. The device of claim 8, wherein the controller measures length of the P waves and upon determining that the length of the P waves is increasing, records data indicative of the potential future dysfunction.

11. The device of claim 8, wherein the controller measures the interatrial conduction delays and upon determining that the length of the interatrial conduction delays exceeds a threshold, records data indicative of the potential future dysfunction.

12. The device of claim 8, wherein the dysfunction comprises one or more of atrial fibrillation, mitral regurgitation (MR) and left ventricle (LV) dysfunctions/remodeling.

13. A implantable cardiac stimulation device comprising:
   at least one lead adapted to be implanted within a patient so as to be able to deliver therapeutic stimulation to the patient's heart;
   at least one sensor that is adapted to sense signals indicative of atrial activity of the heart of the patient; and
   a controller that receives signals indicative of the atrial activity of the heart from the at least one sensor and processes the sensed signals to determine an interatrial conduction delay, wherein the controller selectively induces delivery of therapeutic stimulation to the heart of the patient via the at least one lead, and wherein the controller evaluates a timing parameter related to the interatrial conduction delay from the atrial signals to determine if the signals are indicative that one or both conditions exist of heart failure (HF) worsening or the heart potentially developing a future fibrillation condition and wherein the controller records data indicative of the potential future fibrillation condition upon determining that the data is indicative thereof; and wherein the at least one timing parameter of the atrial signals comprises one or more of a P wave duration and an interatrial conduction delay sensed at a left atria (LA).

* * * * *